United States Patent
Conolly et al.

(10) Patent No.: US 7,502,640 B2
(45) Date of Patent: Mar. 10, 2009

(54) POSITIVE CONTRAST MRI OF MAGNETICALLY TAGGED CELLS, OBJECTS, TISSUES

(75) Inventors: Steven M. Conolly, Palo Alto, CA (US); Charles H. Cunningham, San Francisco, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 912 days.

(21) Appl. No.: 10/849,068

(22) Filed: May 18, 2004

(65) Prior Publication Data

US 2005/0261575 A1 Nov. 24, 2005

(51) Int. Cl.
*A61B 5/055* (2006.01)

(52) U.S. Cl. .............. 600/411; 600/410; 600/424; 600/420; 424/9.1; 424/9.3; 424/9.323; 324/201; 324/204; 324/214; 324/215

(58) Field of Classification Search ............ 600/410, 600/420, 424, 431, 411; 324/201, 204, 214, 324/215, 307, 309; 424/9.3, 9.323, 9.1
See application file for complete search history.

(56) References Cited

U.S. PATENT DOCUMENTS

| | | | | |
|---|---|---|---|---|
| 5,352,979 | A | * | 10/1994 | Conturo ................ 324/307 |
| 5,415,163 | A | * | 5/1995 | Harms et al. ............ 600/410 |
| 6,630,126 | B2 | * | 10/2003 | Driehuys et al. ......... 424/9.3 |
| 6,963,769 | B1 | * | 11/2005 | Balaban et al. ......... 600/420 |
| 2005/0059881 | A1 | * | 3/2005 | Balaban et al. ......... 600/420 |

OTHER PUBLICATIONS

Cunningham et al. Positive contrast magnetic resonance imaging of cells labeled with magnetic nanoparticles. Magnetic Resonance in Medicine. 53(5):p. 999-1005. May 2005.*
Cunningham et al., "Positive Contrast MRI of Cells Labeled with Magnetic Nanoparticles", Apr. 2004, Accepted for Publication in Magnetic Resonance in Medicine in Fall 2004, 22 pages.
International Search Report and Written Opinion in corresponding PCT Application PCT/US05/17689, mailed Nov. 16, 2006.
Pineda et al., "Cramer-Rao Bounds for Three-Point Decomposition of Water and Fat", Magn Reson Med. Sep. 2005; 54(3):625-635.

* cited by examiner

*Primary Examiner*—Ruth S Smith
*Assistant Examiner*—Parikhas S Mehta
(74) *Attorney, Agent, or Firm*—Beyer Law Group LLP (57) ABSTRACT

Contrast agents incorporating super-paramagnetic iron-oxide (SPIO) nanoparticles have shown promise as a means to visualize labeled cells using MRI. Labeled cells cause significant signal dephasing due to the magnetic field inhomogeneity induced in water molecules near the cell. With the resulting signal void as the means for detection, the particles are behaving as a negative contrast agent, which can suffer from partial-volume effects. Disclosed is a new method for imaging labeled cells with positive contrast. Spectrally-selective RF pulses are used to excite and refocus the off-resonance water surrounding the labeled cells so that only the fluid and tissue immediately adjacent to the labeled cells are visible in the image. Phantom, in vitro, and in vivo experiments show the feasibility of the new method. A significant linear correlation (r=0.87, p<0.005) between the estimated number of cells and the signal has been observed.

17 Claims, 6 Drawing Sheets

POSITIVE CONTRAST MRI OF MAGNETICALLY TAGGED CELLS, OBJECTS, TISSUES

GOVERNMENT RIGHTS

This invention was made with Government support under contract HL067181 awarded By the National Institutes of Health. The Government has certain rights in this invention.

BACKGROUND OF THE INVENTION

This invention relates generally to magnetic resonance imaging (MRI), and more particularly the invention relates to the use of MRI in tracking magnetically labeled cells or objects using positive contrast.

INTRODUCTION

Contrast agents incorporating super-paramagnetic iron-oxide (SPIO) nanoparticles have shown much promise as a means to visualize labeled cells using MRI. The small size of the particles (<100 nm) facilitates transport across cell membranes, and the low toxicity allows for large iron loads without significant cell death (e.g., 25 pg/cell). Labeling can be performed by incubating cells of interest (e.g., embryonic stem cells) with the contrast agent in vitro, so that they can be monitored in vivo using MRI. Cells such as macrophages can be labeled in vivo by introducing the contrast agent into the bloodstream, with the uptake of the agent occurring by phagocytosis, which has been used to image atherosclerosis and other inflammatory processes. In more advanced schemes, SPIO-protein complexes that bind to the receptors on specific cells have been used.

Cells loaded with SPIO cause significant signal dephasing due to the magnetic field inhomogeneity induced in water molecules near the cell. These manifest as signal voids in the image. With the signal void as the means for detection, the particles are behaving as a negative contrast agent, as opposed to positive contrast agents such as gadolinium chelates that brighten the local signal intensity by shortening T1. A fundamental drawback of negative contrast agents is that the agent cannot be distinguished from a void in the image. Moreover, negative contrast agents suffer from partial-volume effects, where the ability to detect a void depends critically on the resolution of the image; voxel size must be smaller than the void volume for reliable visualization. While it is possible to achieve positive contrast with SPIOs by employing T1 weighting, this is only possible with the smaller-sized particles (10-50 nm) and can be inefficient because of competing T1 and T2* effects.

SUMMARY OF THE INVENTION

The present invention is a new method for imaging objects and materials that cause a localized magnetic field inhomogeneity in an MRI scanner with positive contrast. In one embodiment of the new method, spectrally-selective RF pulses are used to excite and refocus the off-resonance water surrounding the cells labeled with SPIO agents, while suppressing on-resonance signal, so that only the fluid and tissue immediately adjacent to the labeled cells are visible in the image.

The invention and object and features thereof will be more readily apparent from the following detailed description and appended claims when taken with the drawings.

DETAILED DESCRIPTION OF THE PREFERRED EMBODIMENTS

Theory

A collection of labeled cells will cast a field pattern in the water molecules immediately surrounding the cells. The field pattern can be approximated by a dipole field from a magnetized sphere. The dipole pattern demonstrates a classic field cross pattern, in which the local $B_z$ field is enhanced in the north and south poles and diminished along the equator. The polarity of the field perturbation would be reversed for a diamagnetic agent. The dipole field pattern intensity falls off quickly. The field perturbation varies as $$\Delta B_z(r, \theta) = \frac{\Delta \chi B_o}{3} \left(\frac{a}{r}\right)^3 (3\cos^2\theta - 1) \quad (1)$$

where $\Delta\chi$ is the difference in bulk magnetic susceptibility between the sphere and surroundings, a is the radius of the sphere, r is the distance from the sphere center, and $\theta$ is the angle relative to the main field, $B_o$. Hence, the field pattern from a smaller collection of cells will fall off more steeply than that from a larger collection. In practice, agglomerations of labeled cells may not be spherical, but this theory can be applied to the general case by summing the patterns from a group of spheres.

Figure 1A:
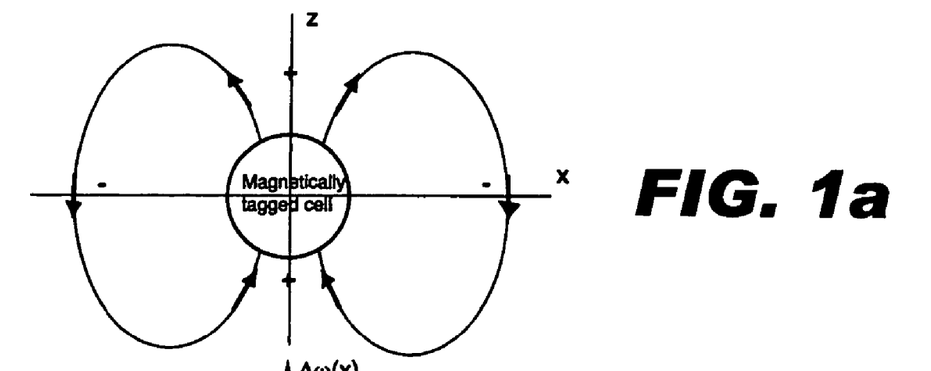
FIGS. 1a-1c illustrate magnetic field lines induced outside a magnetized sphere; regions of excitation for a RF pulse with carrier frequency Ws and bandwidth BW; and isofrequency contours surrounding a magnetized sphere.
Figure 1B:
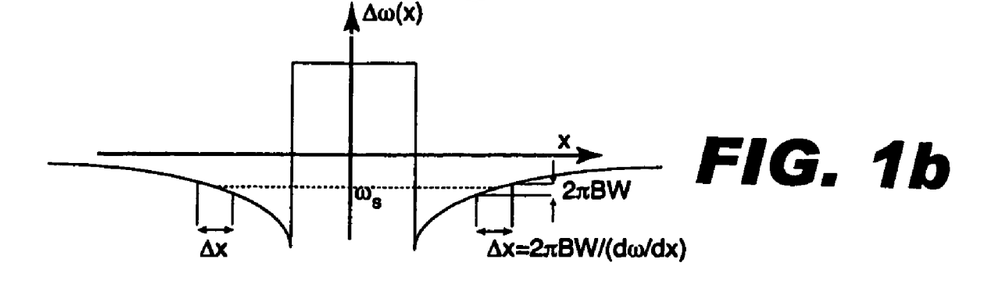
Figure 1C:
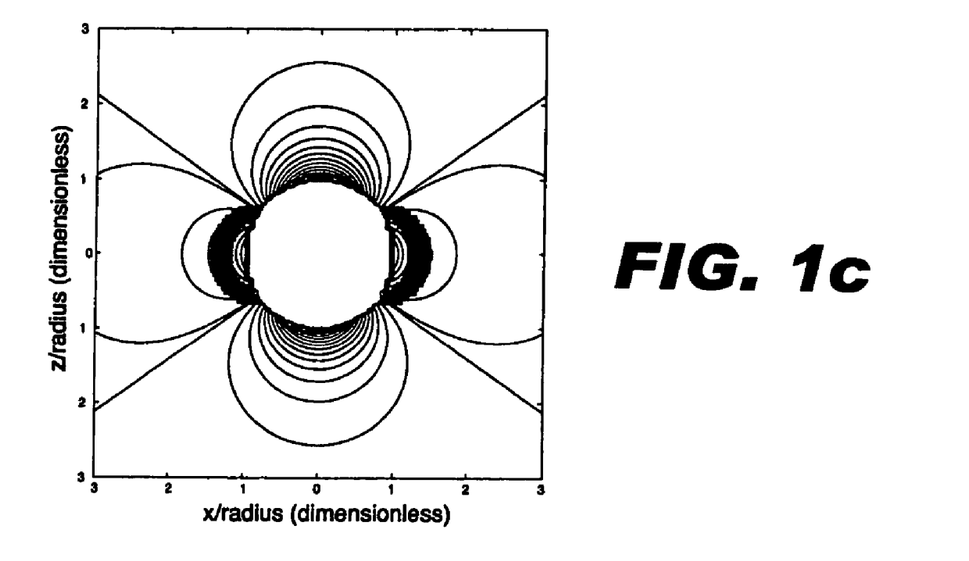

Instead of using the field gradient cast by the labeled cells to de-phase the NMR signal from nearby water molecules, we propose to use this gradient to selectively excite and refocus a narrow band of water molecules. This is similar in concept to slice-selective excitation, where a narrowband RF pulse is applied in the presence of a linear field gradient to select a particular slice. There are some notable differences: the field cast by a labeled cell is extremely localized and nonlinear. However, the pulse sequence is designed to extend the slice-selection concept to excite/refocus a thin shell of spins located at a particular frequency offset from the magnetized cells. FIG. 1 illustrates the concept. In FIG. 1(a), the magnetic-field lines induced outside a magnetized sphere. In FIG. 1(b), by applying an RF pulse with center-frequency shift $\omega_s$ and bandwidth BW, the regions with thickness $\Delta x$ are excited. In FIG. 1(c), isofrequency contours surrounding a magnetized sphere ($\Delta\chi$=−500 ppm) are shown, with the shaded regions showing the spatial extent of the regions that would be excited by a band-selective RF pulse with $\omega_s$=–150 ppm and BW=100 ppm. Similar to conventional slice selection, a spatial shell of water is excited using the intense microgradient. Since only this shell is excited, the image demonstrates positive contrast. Note that positive frequency shifts will excite spins at the poles (where the field is enhanced) and negative frequency shifts will excite spins at the equator (where the field is diminished). A symmetric (cos-modulated) RF pulse will excite both the poles and the equator. The spatial distribution of this signal will be that of an "onion layer". Note that in conventional slice selection the gradient is refocused by a negative lobe of half the duration. Because it is impossible to negate the gradient due to a magnetic particle, spin-echo refocusing pulses are currently thought to be critical.

The theory above can be used to predict the net signal resulting from the new method, as a function of the volume of labeled cells. For a spin to contribute signal, its resonant frequency must fall within the bandwidth of the selective RF pulses:

$$|\gamma \Delta B_z - \omega_s| \leq 2\pi \frac{BW}{2} \quad (2)$$

where $\omega_s$ is the center-frequency shift of the RF pulses and BW is the bandwidth of the RF pulses. Substituting Eq. 1 for $\Delta B_z$ gives:

$$\left| \frac{\gamma \Delta \chi B_o}{3} \left(\frac{a}{r}\right)^3 f(\theta) - \omega_s \right| \leq 2\pi \frac{BW}{2} \quad (3)$$

Now, the surfaces of the volume that satisfies Eq. 3 can be parameterized as follows:

$$\frac{r_i}{a} = K_i(\theta) \quad (4)$$

$$\frac{r_o}{a} = K_o(\theta)$$

where $r_i$ is the radius from the center of the sphere to the inner surface of the volume, and $r_o$ is the radius to the outer surface. From this it is seen that the distance between the two surfaces, along a radius, scales with a:

$$r_o - r_i = a(K_o(\theta) - K_i(\theta)) \quad (5)$$

Thus all three dimensions of the volume defined by Eq. 3 scale with a, resulting in a signal volume that scales as $a^3$. Since the volume of cells also scales as $a^3$, this analysis predicts a linear relationship between the volume of cells and integrated signal.

There are several pulse-sequence parameters that can affect the quality of the positive contrast images. The key parameters are: the excitation profiles' shape (bandwidth, transition width, ripples), the center-frequency shift, and the echo time. These parameters are linked and the tradeoffs are discussed below.

The excitation profiles of the frequency selective RF pulses must be carefully designed to achieve good contrast-to-noise. For a fixed bandwidth of excitation pulses, the largest volume of water will be excited for each cell by minimizing the off-resonance shift, as shown in FIG. 1. This excites the largest-radius shell of tissue or fluid. However, there is a tradeoff in contrast: if the frequency is set too close to on-resonance water, then excitation of background spins could occur because water could be shifted into the passband by field inhomogeneities. For adequate background suppression, the "out-of-slice" ripple of the RF pulses is also a concern. These ripples can be made small at the expense of wider transition widths.

For fixed off-resonance frequency, the bandwidth of the RF pulses determines the thickness of the shell excited. For a maximal volume of magnetization, the excitation bandwidth would be set as wide as possible. It is because of this wide bandwidth that the T2* decay is rapid and a spin-echo sequence is crucial. However, there is a tradeoff because wide bandwidth implies that the T2* decay of the spin echo will be extremely short, which will limit sensitivity and resolution. Hence a different, optimal RF bandwidth for different sized groups of cells is expected.

Another important challenge is diffusion: the field gradient immediately outside a single, small SPIO particle is enormous. Diffusion of the excited water molecules near the labeled cells could cause significant, irreversible signal dephasing. However, it is known that with conventional pulse sequences, the signal loss in vicinity of sufficiently loaded cells is governed by the "static dephasing regime" theory, in which diffusional losses are minor. Since the new method images spins which are not visible with conventional methods, the appropriate theoretical model for the relaxation properties of these spins remains unclear. In theory, the effects of diffusion can be reduced by minimizing both the center-frequency shift and the echo time. A potential tradeoff exists because longer RF pulses can excite sharper profiles, and can therefore be moved closer to resonance (where the gradients are less steep), but the increase in echo time could increase diffusion losses.

Although we have identified many potential tradeoffs above, we have not yet attempted to find an optimal combination of parameters. Instead, a particular combination of parameters was used that enabled the demonstration of the new method in the experiments described below.

Methods

Figure 2:
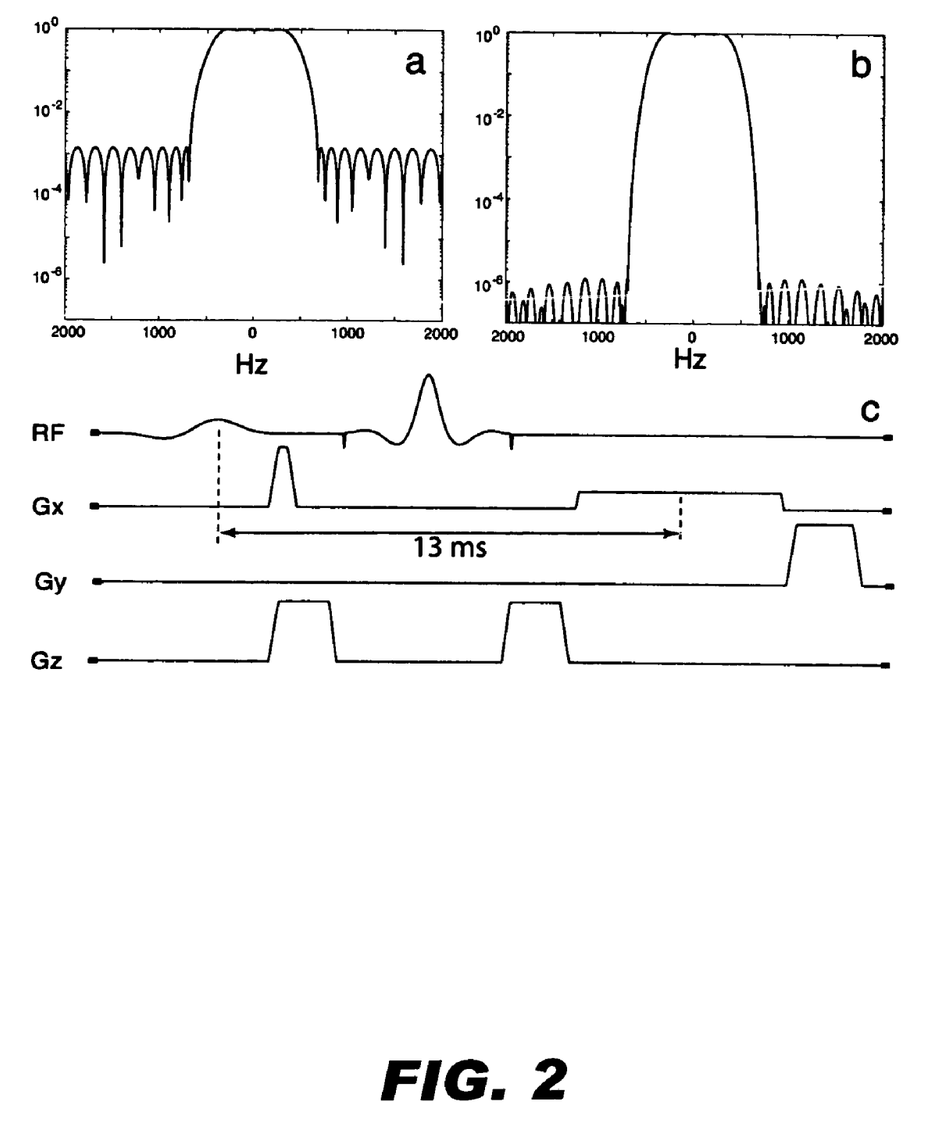
FIG. 2 illustrates a pulse sequence for positive-contrast imaging of tagged cells in accordance with an embodiment of the invention and a pulse sequence for a minimum echo line with short readout to minimize blurring associated with a wideband echo.

Spectrally-selective RF pulses were designed using the Shinnar-Le Roux (SLR) algorithm implemented in MATLAB (The Mathworks Inc., Natick, Mass.). By matching the profiles of a 90-degree excitation and a 180-degree refocusing pulse, a spin-echo sequence with million-fold (120 dB) suppression of on-resonance water was designed as shown in FIG. 2. FIG. 2 shows a pulse sequence for positive-contrast imaging of magnetically tagged cells. (a) The profile for each of the 5 ms RF pulses was designed to excite/refocus a 1 kHz passband with 0.1% out-of-slice ripple. (b) The profile for the combined 90-180 pair gives million-fold suppression of on-resonance water. (c) The pulse sequence allows a minimum echo time of 13 ms, with a short (4 ms) readout to minimize the blurring associated with the wideband echo. This pulse sequence was implemented on a GE Signa 1.5T whole-body MRI system (General Electric Medical Systems, Waukesha, Wis.).

Cell labeling solution was prepared by mixing cell culture medium with 25 µg/mL of the SPIO Feridex (Advanced Magnetics, Cambridge, Mass.) and 375 ng/mL of poly-l-lysine (Sigma, St. Louis, Mo.) at room temperature for 60 minutes. The embryonic stem cell (ESC) line TL-1 was derived from 129Sv/J mice and cultured in a medium consisting of high-glucose Dulbecco's modified Eagles Medium with L-glutamate (Specialty Media, Pillipsburg, N.J.), 10% ESC qualified fetal bovine serum (Invitrogen, Carlsbad, Calif.), and 1% penicillin/streptomycin solution (Invitrogen, Carlsbad, Calif.). Prior to injection, the cells were incubated with the labeling solution for 12-24 hours. The cell cultures were then transferred to centrifuge tubes and subjected to three cycles of centrifuge, each time followed by dilution with phosphate-buffered saline solution to wash away any extracellular SPIO.

For initial testing of the sequence, cells were injected into a rectangular block of agar gel. Because of concerns about diffusion, groups of cells were injected in the near-solid form resulting from centrifuge spinning without dilution. The cells were injected using a syringe with 5 mL capacity, with an estimation of the number of cells injected made from the volume-measurement markings printed on the syringe. Groups of three different cell populations ($3 \times 10^6$, $1 \times 10^6$, $0.5 \times 10^6$) were injected, and effort was made to avoid inclusion of air pockets. Imaging was performed using the sequence illustrated in FIG. 2 with TR=800 ms, TE=14 ms, FOV=12 cm, and 256×128 2DFT encoding with an 8 ms readout. The whole-body RF coil was used for transmission and a 5 inch surface coil for reception. To change the frequency range included in the passband of the RF pulses, the center frequency of the scanner (both excite and receive) was shifted. Projection images were acquired at 0 Hz, +800 Hz and −800 Hz shifts. For comparison, standard multislice gradient-echo images were acquired with TR=100 ms, TE=8 ms, FOV=12 cm, 256×192 encoding, and 2 mm slice thickness.

To test the new method in the presence of more realistic diffusion parameters, groups of cells were imaged after injection into a section of freshly excised porcine myocardium. The cells were diluted to a concentration of approximately $10^8$ cells/mL, and four injections of 1 million cells were performed. The same imaging parameters, sequences, and coils as listed above were used. Also, additional images were acquired with the new sequence set at −800 Hz with echo times ranging from 14 ms to 34 ms to investigate diffusion effects.

Finally, a group of approximately 1 million cells was injected into the hind limb of a live mouse at a concentration of $10^7$ cells/mL. The mouse was studied under a protocol approved by the Stanford University Administrative Panel on Laboratory Animal Care. The mouse was anesthetized with an intraperitoneal injection of 12% ketamine (Wyeth, Madison, N.J.) and 4% xylazine solution (Phoenix Pharmaceuticals, St. Joseph, Mo.) and allowed to breathe spontaneously. The concentration of the anesthetic solution was kept within the 100-120 μL/g dosing range. Imaging was performed approximately 45 minutes after the injection. The same imaging parameters, sequences, and coils as described above were used, except with an 8 cm FOV.

Results

Figure 3:
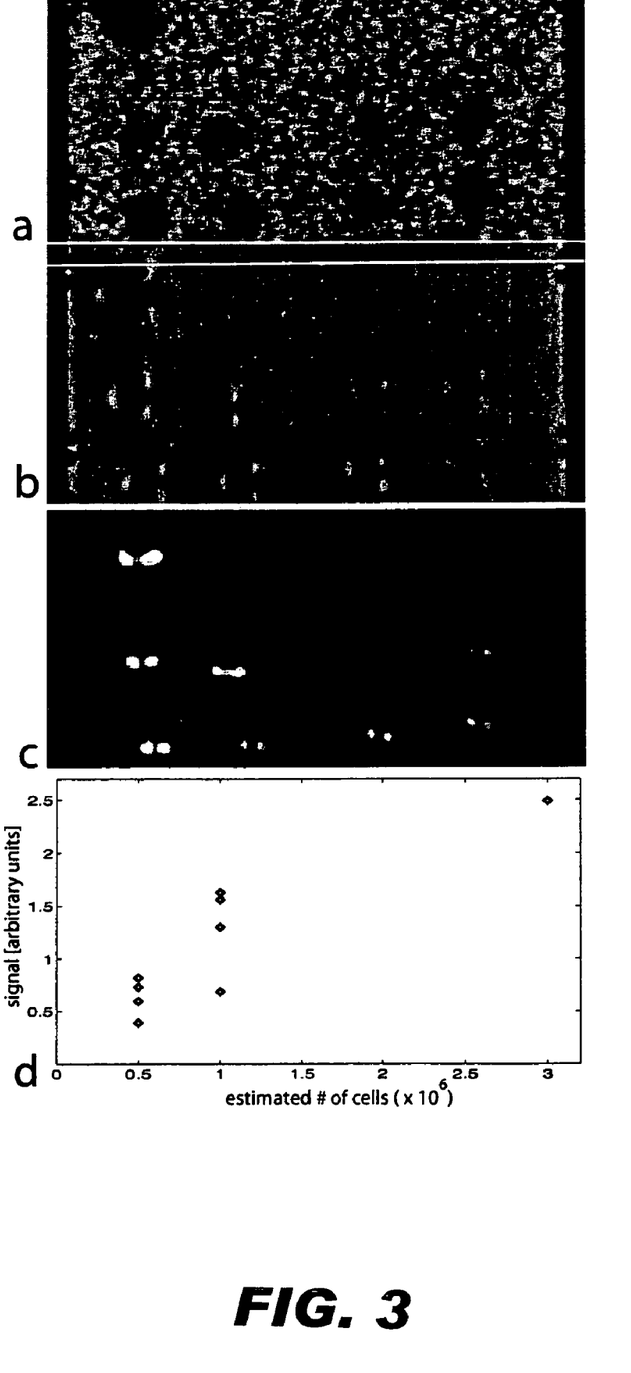
FIG. 3 is a comparison of off-resonance imaging of magnetically labeled cells and conventional gradient-echo images.

The phantom experiment in FIG. 3 shows initial investigations into the minimum detectable number of cells and the correlation between signal and the number of cells injected. FIG. 3 shows a comparison of off-resonance imaging of magnetically labeled cells and conventional gradient-echo images. The phantom was a slab of agar gel with a plastic grid (1 cm squares) included for landmarking. (a) The gradient-echo images show voids at the injection sites of 3 million cells (1), 1 million cells (2), and 0.5 million cells (3). (b) The on-resonance projection also shows voids, but with less contrast due to background signal. (c) The off-resonance projection (−800 Hz) shows excellent contrast. (d) Plot of the signal shown in (c) is computed by summing the signal in a small ROI containing each bright spot, vs. the estimated number of cells. The signal at the site of each injection was computed by summing the signal in a rectangular ROI containing the injection site, consisting of 230 pixels. A significant linear correlation between the estimated number and the signal was observed (r=0.87, p<0.005), which agrees with the Theory. Injections of $5 \times 10^5$ cells were easily detected, suggesting that the limit of the method is lower. The shape of bright regions in FIG. 3(c) agrees with theory, with signal emanating from the right and left of the injection (along an axis perpendicular to the main field) where the magnetic field is suppressed (see FIG. 1).

Figure 4:
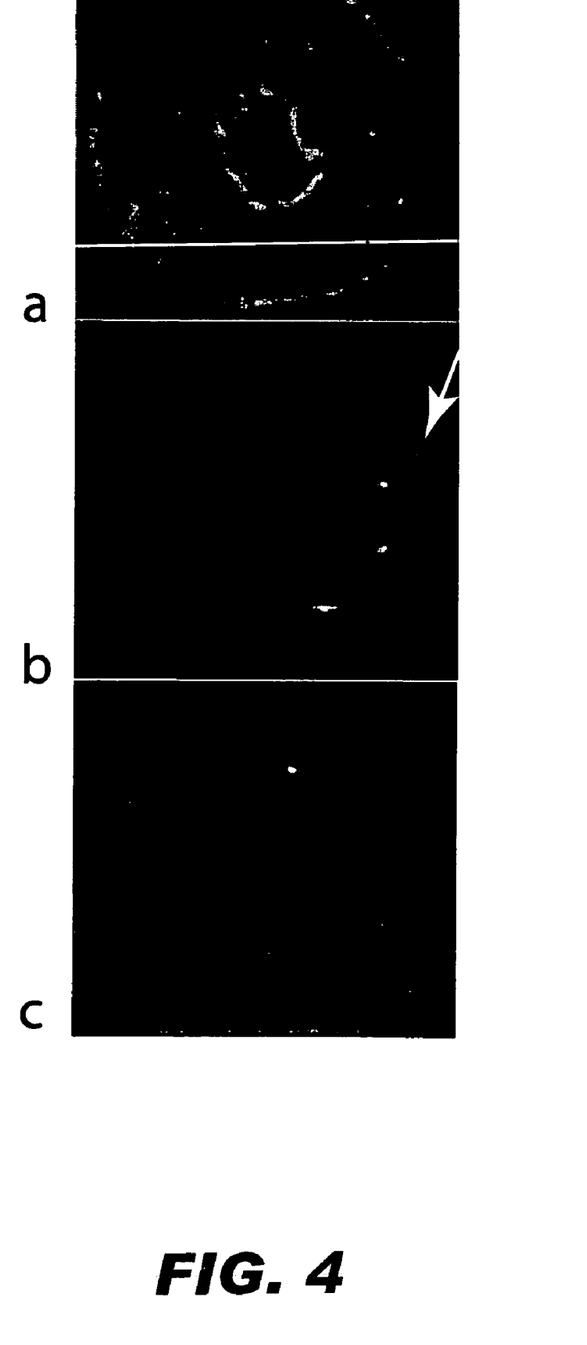
FIG. 4 illustrates a test of positive-contrast imaging in vitro using a) gradient-echo images; b) off-resonance projection at −800 Hz and c) off-resonance projection at +800 Hz.
Figure 5:
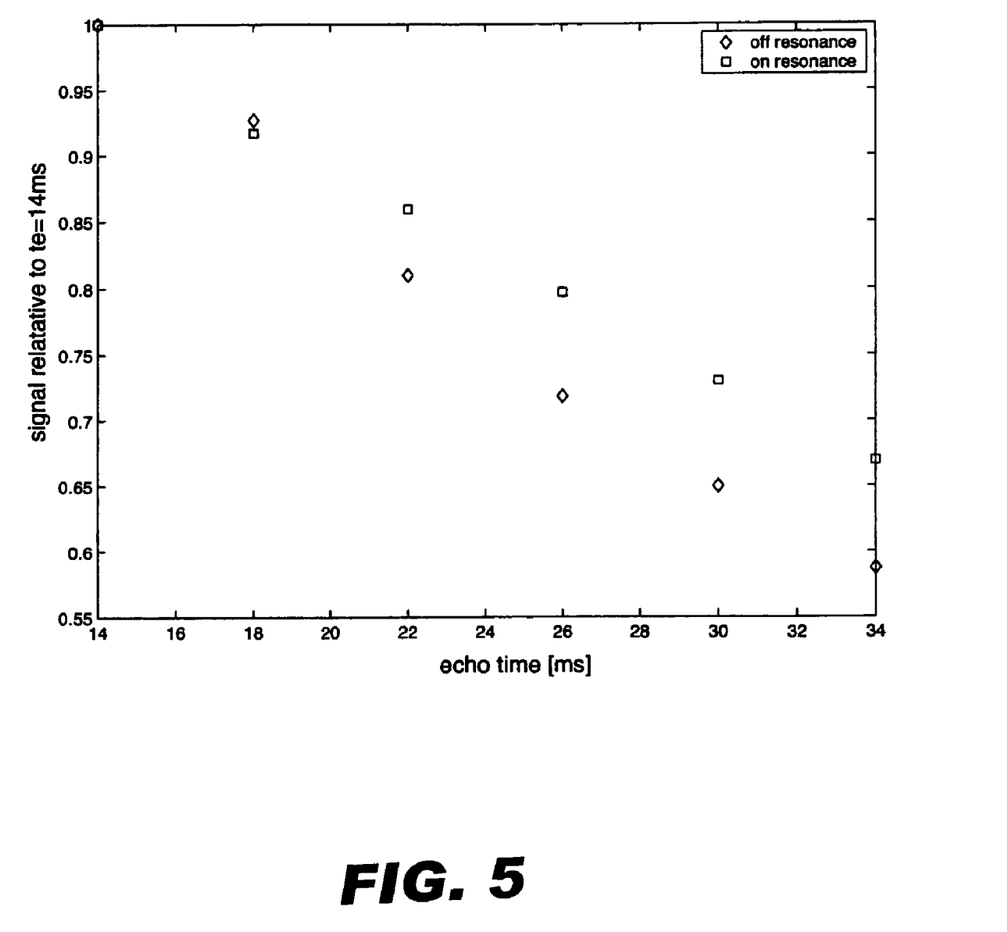
FIG. 5 is a graph illustrating the effect of echo time on off-resonance signal.

The potential signal loss due to diffusion was investigated in the experiments shown in FIG. 4 and FIG. 5. FIG. 4 shows a test of positive-contrast imaging in vitro. A section of porcine myocardium injected with labeled cells is shown. (a) Gradient-echo images show voids at each injection site of 1 million labeled cells. (b) The off-resonance projection at −800 Hz clearly shows the four injections of labeled cells. (c) The off-resonance projection at +800 Hz also shows the injections, with the signal located at the top and bottom of each injection as predicted by theory. There is also a region of positive contrast (arrow) that is not at an injection site, but does correlate with a small void in (a). This was likely due to leakage of labeled cells through a blood vessel. The images are cropped to 7 cm×7 cm. FIG. 5 illustrates the effect of echo time on the off-resonance signal. The mean signal inside an ROI containing an injection of 1 million cells into porcine myocardium is shown. The same ROI for the on-resonance and off-resonance (−800 Hz) was used. The difference in slope between the two curves is possibly due to diffusion losses in the gradient field surrounding the cells. The diffusion coefficient within the excised myocardium can be assumed to be similar to that encountered in vivo. Thus, the reasonable signal observed at an echo time of 14 ms indicates that diffusional losses are not a major limitation for this number of cells. The apparent T2 of the off-resonance water surrounding the cells was found to be slightly shorter than that of the on-resonance water (FIG. 5), and this is presumed to be due to diffusion effects.

Figure 6:
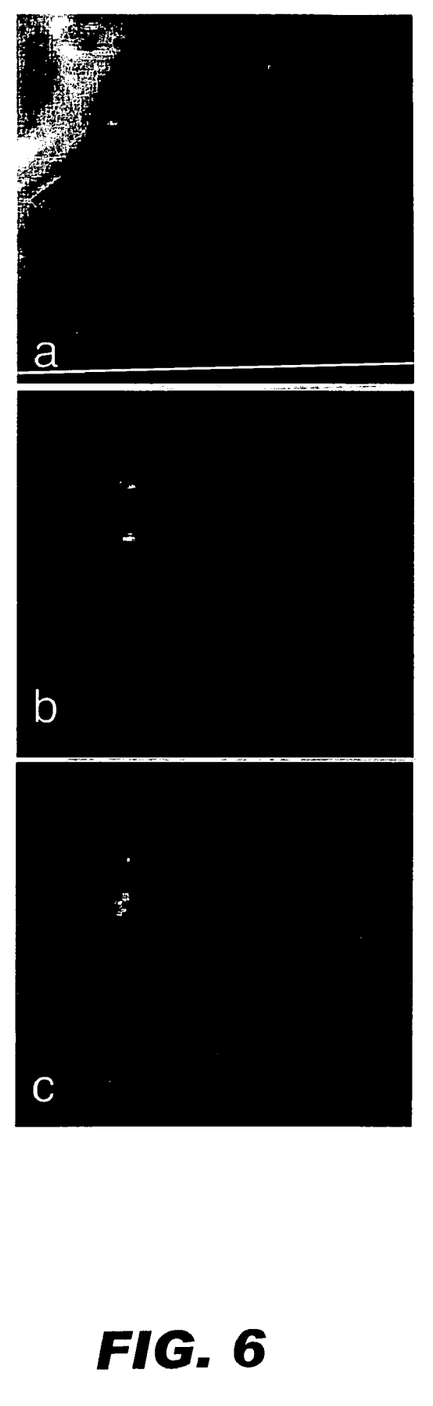
FIG. 6 illustrates positive contrast in vivo.

The in vivo experiment shown in FIG. 6 demonstrates that the new method is feasible even when the cells are injected at a fairly low concentration ($10^7$/mL), which was feared to increase diffusional signal loss. In FIG. 6 labeled cells were injected into the hind limb of a mouse. The on-resonance spin-echo image shows a slight artifact at the location of the injection (arrow). (b) The spin-echo image at −800 Hz shows positive contrast at the corresponding location. The spin-echo image at +800 Hz shows signal at a similar location, but with different geometry due to the fact that a different part of the dipole field is being excited/refocused. The images are cropped to 2.8 cm×3.0 cm. This is an important result as dilute cell suspensions may be needed to minimize cell damage at the time of delivery. In this experiment, the new method was applied 45 minutes after the cell injection, so it is reasonable to assume that some absorption of the fluid into the surrounding tissue had occurred.

Discussion

The results shown in FIG. 3 to FIG. 6 demonstrate the feasibility of the new method. In all cases, the new method gave positive contrast at the sites where the labeled cells were injected. The imaging of a contiguous group of labeled cells with positive contrast is anticipated to be useful for quickly visualizing and landmarking after an injection. This may be particularly useful when a small receiver coil with a small volume of sensitivity is used, giving a large intensity variation across the image and making voids difficult to detect. Conventional, negative-contrast scans could then be prescribed from the positive contrast projection.

The correlation between the signal and the number of cells shown in FIG. 3 provides hope that quantification of labeled cell volume will be simpler with the new method in comparison with the conventional, negative contrast methods. Based on these results, it seems feasible to estimate the volume of cells with the new method immediately after injection, simply by summing the pixels in an ROI. However, if the goal were to follow the volume of cells over time, quantification might not be so simple. In this case, cell division will reduce the concentration of contrast agent within each cell, which will undoubtedly change the signal characteristics.

The pulse sequence presented here is simple. One obvious extension to this method is to employ spectral-spatial selective excitation to enable the excitation of the desired frequency band, while also restricting the excitation to a spatial slice. This would reduce the level of background suppression required, because less on-resonance water would be inside the spatial region affected by the RF pulse. Also, a better shim can be achieved over a 2-dimensional slice, with the possibility of shimming each individual slice in a multislice approach.

Another improvement to the method would be to reduce the echo time. This could be essential for using the method to image a group of labeled cells over a long period after injection. In this case, the cells may divide, reducing the amount of contrast agent in each cell, and migrate so that labeled cells are distributed amongst non-labeled cells. With smaller groups of cells, the magnetic field gradient surrounding the cells becomes larger, and signal dephasing due to diffusional motion becomes more of a concern.

We have presented a new method for imaging magnetically labeled cells in vivo with positive contrast. Positive contrast has inherent advantages over existing negative contrast techniques, which suffer from partial voluming and hence require high resolution. The experiments described here show the feasibility of the method. The signal from the off-resonance water surrounding labeled cells was shown to correlate with the number of cells. The T2 of the signal from the new method was slightly shorter than that from the on-resonance water in the same location. However, the in vivo experiment demonstrated that this will not be a major limitation, at least for large numbers of cells. The new method is anticipated to be useful for quickly visualizing the location of a cell injection, and for quantifying the volume of labeled cells.

While the invention has been described with reference to specific embodiments, the description is illustrative of the invention and is not to be construed as limiting the invention.

In one embodiment of the invention, the spin echo created by the sequence is achieved with only one RF pulse, instead of two. This can be accomplished by implementing a "self-refocusing" RF pulse, which creates it's own spin echo. This embodiment will allow shorter echo times than would otherwise be possible, reducing the effects of diffusion and making the method more sensitive.

In another embodiment of the invention, the 90-degree and/or 180-degree pulse are replaced with spectral-spatial RF pulses, making slice selection with the new method possible.

In another embodiment of the invention, the above two embodiments are combined with the envelope of the spectral-spatial RF pulse designed to be self-refocusing. This will enable slice selection as well as shorter echo times than can be achieved with a conventional spin-echo sequence.

In another embodiment of the invention, multiple images are acquired with the frequency offset of the sequence varied over a range including both positive and negative shifts relative to water. Then, spatial correlation of the image signal is used, either by an automatic algorithm or by a human, to compute the location, volume and spatial configuration of the labeled material.

In another embodiment of the invention, the source of the magnetic field inhomogeneity is not a group of labeled cells, but instead any object or material with magnetic susceptibility sufficiently different from water, which can be placed inside the body. For example, a catheter or guidewire with a tip having a susceptibility sufficiently different from water could be visualized using the invention.

Various modifications and applications may occur to those skilled in the art without departing from the true scope and spirit of the invention as defined by the appended claims.

What is claimed is:

1. A MRI method for identifying the presence and location in a body of a contrast agent or an object with magnetic susceptibility sufficient to induce magnetic field inhomogeneity in water molecules near the agent or object comprising the steps of:
   a) administering a contrast agent or object to the body, wherein the agent or object has a magnetic susceptibility that causes a magnetic field shift in the portions of the body which are in the vicinity of the contrast agent or object,
   b) placing the body in a static magnetic field,
   c) applying a sequence of RF excitation or refocusing pulses or RF excitation and refocusing pulses to excite or focus or excite and focus a narrow band of frequencies centered about a resonant frequency corresponding to the magnetic field shift whereby only water molecules near the contrast agent or object experience a magnetic field shift and are excited by the RF excitation pulse,
   d) detecting water molecules experiencing the magnetic field shift, and
   e) forming an image from the detected water molecules experiencing the magnetic field shift thereby permitting location of the contrast agent or object with magnetic susceptibility.

2. The method of claim 1 wherein in step c) the narrow band of frequencies is off resonance for water molecules not experiencing the magnetic field shift whereby water molecules not experiencing the magnetic field shift are not excited.

3. The method of claim 2 wherein the sequence of RF excitation or refocusing pulses use gradient magnetic fields and is spectrally and spatially selective.

4. The method of claim 3 wherein the bandwidth of the RF excitation pulse sequence is selected to limit the magnetic-field shifted water molecules.

5. The method of claim 4 wherein the sequence of RF excitation or refocusing pulses is self refocusing for creating a spin-echo signal from the excited water molecules.

6. The method of claim 5 wherein the spin-echo time is selected to limit effects of water molecule diffusion.

7. The method of claim 6 wherein the spin-echo time is dependent on excitation close to the center frequency of the RF signal.

8. The method of claim 7 wherein in step c) a gradient-echo sequence is employed for excited water molecule signal detection.

9. The method of claim 8 wherein in step c) a large-amplitude readout gradient is employed in detection to reduce blurring associated with a wide band of frequencies surrounding the contrast agent.

10. The method of claim 1 wherein the RF excitation pulse sequence includes a 90-degree pulse and a 180-degree refocusing pulse.

11. The method of claim 10 wherein a spin-echo time is selected to limit effects of water molecule diffusion.

12. The method of claim 11 wherein the spin-echo time is dependent on excitation close to the center frequency of the RF signal.

13. The method of claim 12 wherein in step c) a gradient-echo sequence is employed for excited water molecule signal detection.

14. The method of claim 13 wherein in step c) a large-amplitude readout gradient is employed in detection to reduce blurring associated with a wide band of frequencies surrounding the contrast agent.

15. The method of claim 1 wherein multiple images are acquired with a frequency offset of the RF pulses varied over a range including both positive and negative frequencies relative to water.

16. The method of claim 15 where spatial correlation is used to compute the location, volume and configuration of the magnetic material.

17. The method of claim 1 where the object is a catheter or guidewire with a tip that is manufactured from a material with susceptibility sufficiently different form water such that it is visible with the method.

* * * * *

UNITED STATES PATENT AND TRADEMARK OFFICE
CERTIFICATE OF CORRECTION

| | | |
|---|---|---|
| PATENT NO. | : 7,502,640 B2 | Page 1 of 1 |
| APPLICATION NO. | : 10/849068 | |
| DATED | : March 10, 2009 | |
| INVENTOR(S) | : Conolly et al. | |

It is certified that error appears in the above-identified patent and that said Letters Patent is hereby corrected as shown below:

In the Specification Under Column 1:

• Please replace Column 1, line no. 7-9 with:

-- FEDERALLY-SPONSORED RESEARCH OR DEVELOPMENT
This invention was made with Government support under contract HL067161 awarded by the National Institutes of Health. The Government has certain rights in this invention. --

Signed and Sealed this
Seventeenth Day of September, 2013

Teresa Stanek Rea
*Deputy Director of the United States Patent and Trademark Office*